United States Patent [19]
Dar et al.

[11] Patent Number: 5,995,212
[45] Date of Patent: Nov. 30, 1999

[54] SYSTEM AND METHOD FOR INSPECTING AN OPTICAL FIBER INCLUDING AN EPOXY AREA SURROUNDING THE OPTICAL FIBER

[75] Inventors: Iqbal M. Dar, Odenton; Qiong Zhan, Ellicott City; Andrei Csipkes, Savage, all of Md.

[73] Assignee: CIENA Corporation, Lenthicum, Md.

[21] Appl. No.: 09/123,434

[22] Filed: Jul. 28, 1998

[51] Int. Cl.$^6$ .................................................. G01N 21/00
[52] U.S. Cl. ................................................ 356/73.1; 356/237
[58] Field of Search ................................... 356/73.1, 237

[56] References Cited

U.S. PATENT DOCUMENTS

| | | |
|---|---|---|
| 4,721,357 | 1/1988 | Kovalchick et al. ................. 350/96.2 |
| 4,787,698 | 11/1988 | Lyons et al. ........................... 350/96.2 |
| 5,179,419 | 1/1993 | Palmquist et al. . |
| 5,729,622 | 3/1998 | Csipkes et al. . |
| 5,809,162 | 9/1998 | Csipkes et al. . |

Primary Examiner—Reginald A. Ratliff
Attorney, Agent, or Firm—David L. Soltz

[57] ABSTRACT

A system and method for inspecting an optical fiber, particularly an epoxy region of an optical fiber in a supporting structure. The inspection may use an initialization routine including determination of whether the centering between the optical fiber and the illumination source is sufficient. The meters used to determine completion of initialization may be displayed. The inspection may analyze the uniformity of the thickness of an epoxy layer between the fiber and the supporting structure. The inspection may also analyze the core and clad zones of the optical fiber for scratches and other intensity variations, referred to generically as blobs. The core zone preferably encompasses a region larger than the core alone, e.g., an area which is a multiple of the core diameter. Different criteria are established for the core and clad zones, with no discontinuities being tolerated in the core zone. Scratches may be extracted using a windowing technique. The clad zone has a two-dimensional discrimination factor for both scratches and blobs, one dimension being cumulative for a totality of the intensity variations and the other dimension being for each individual intensity variation. The effect of the illumination of the core on the discrimination may be accounted for.

30 Claims, 10 Drawing Sheets

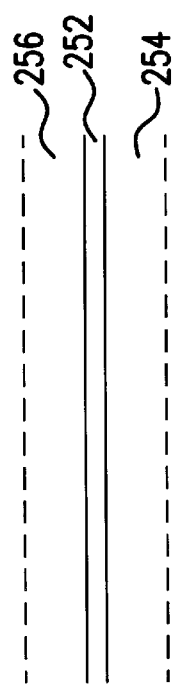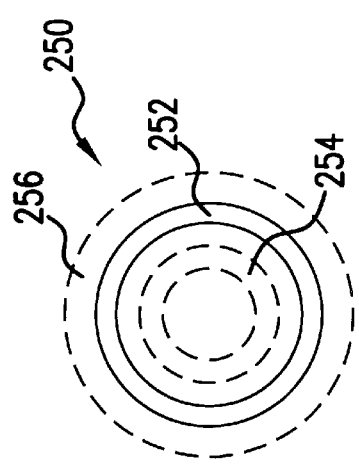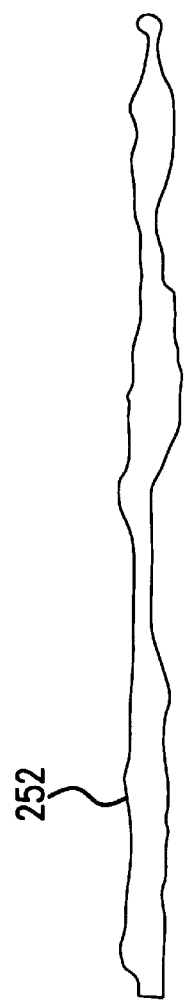
FIG. 6B
FIG. 6D
FIG. 6A
FIG. 6C
FIG. 6E

SYSTEM AND METHOD FOR INSPECTING AN OPTICAL FIBER INCLUDING AN EPOXY AREA SURROUNDING THE OPTICAL FIBER

BACKGROUND OF THE INVENTION

1. Field of the Invention

The present invention is directed generally to a system and method for inspecting an optical fiber. More particularly, the present invention is directed to automating the inspection of an optical fiber, advantageously including inspecting an epoxy area surrounding the optical fiber, while providing repeatability of the inspection, simplicity of assessing results of the inspection, and insuring, upon passing the inspection, a high-quality, durable fiber.

2. Description of Related Art

Optical fibers are widely employed to transmit light for many applications. The demand for inexpensive, reliable, high-performance optical fibers continues to grow.

A cross-section of a typical optical fiber is shown in FIG. 1. The optical fiber includes a core region 102 surrounded by a cladding region 104. Both the core region 102 and the cladding region 104 may be manufactured out of glass. The core region 102 is typically very small, e.g., about four to nine microns in diameter for a single mode fiber. The cladding region 104 typically has a larger diameter than the core region, e.g., about 125 microns in diameter. The cladding region 104 may be surrounded by a supporting structure or ferrule region 108 which protects the core region 102 and the cladding region 104 from damage. The ferrule region 108 may be made of zirconia and may be approximately 2500 microns in diameter. The ferrule region 108 may be attached to the cladding region 104 by an epoxy layer 106.

In order to insure good performance of the optical fiber, the optical fiber needs to be relatively free of defects such as scratches, blobs, cracks, chips, pits, dirt, and other discontinuities/irregularities. The presence of such defects in the optical fiber, particularly in the core region, may result in at least one of increased insertion loss, poor return loss, and premature failure due to the increase of the regions having defects. This increase in the regions having defects may be the result of environmental or mechanical stresses.

Initially, optical fibers were inspected manually by viewing them under a microscope. Such manual inspection has the obvious drawbacks of being time consuming, subjective, not very repeatable, and limited by human visual acuity.

U.S. Pat. No. 5,179,419 discloses a method for detecting, classifying and quantifying defects in an optical fiber. This method provides quantitative information regarding the discontinuities on the optical fiber, but does not provide a qualitative guide for a user. Thus, while the inspection itself is automated, the ultimate conclusion of acceptability of the optical fiber is left to the user. The generation of all of the quantitative information is also quite time consuming.

Another problem with both automated and manual inspection systems is the reliability in terms of repeatability. In other words, the same inspection performed on the same fiber may yield different results.

Further, now that optical fibers have been in use for many years, some of those optical fibers inserted into ferrules or other supporting structures which initially were deemed acceptable have begun to fail. With the increasing use of optical fibers in ferrules or other supporting structures, there is also a need to assess additional long term performance of these optical fibers. One such factor in determining long term performance is the evenness of a layer used to secure the fiber in the supporting structure and to eliminate any resulting gap between the supporting structure and the fiber inserted therein, herein referred to as an epoxy layer. Current approaches for analyzing end surfaces do not take into account the long term effect of any uneven distribution of the epoxy layer or even suggest how to reliably analyze the epoxy layer.

SUMMARY OF THE INVENTION

The present invention is therefore directed to an inspection system and method for optical fibers which substantially overcomes one or more of the problems due to the limitations and disadvantages of the related art.

It is another object of the present invention to provide an inspection method and system for optical fibers which requires the core to be free of intensity variations, while tolerating some intensity variations in the cladding region.

It is yet another object of the present invention to provide an inspection system and method which uses software algorithms to provide real-time processing.

It is still another object of the present invention to provide an inspection system and method which provide a qualitative determination for a user.

It is further an object of the present invention to provide an inspection system and method for optical fibers which has good repeatability and fully removes operator subjectivity.

It is another object of the present invention to provide an inspection system and method for optical fibers in supporting structures which can assess long term performance. In particular, it is an object of the present invention to account for the known physical fact that an uneven epoxy distribution between the fiber and the supporting structure can leave uncured residuals which greatly reduce the reliability of the optical interface, especially over an extended period of time.

It is another object of the present invention to indicate the acceptability of illumination parameters of the fiber, particularly prior to the start of inspection.

One or more of the above, as well as other, objects may be realized by a method for inspecting an optical fiber in a supporting structure including analyzing a thickness of an epoxy layer between the optical fiber and the supporting structure and determining acceptability of the optical fiber in accordance with the analyzing. The analyzing may include imaging the epoxy layer. The supporting structure may be a ferrule and the imaging may include imaging the ferrule and the epoxy layer. The analyzing may include unpolarizing an image of an annulus formed by the epoxy layer. The analyzing may include calculating statistical parameters regarding a variation in the thickness of the epoxy layer around the optical fiber.

One or more of the above, as well as other, objects may be realized by a method for determining centering of an optical fiber relative to an illumination source including comparing illumination levels between at least three points around a periphery of the optical fiber and determining whether centering of the optical fiber relative to the illumination source is within a predetermined level. When the determining indicates that the centering is not within the predetermined level, the optical fiber and the illumination source may be moved relative to one another. The determining may include generating a standard deviation between an average of the illumination levels at the at least three points.

One or more of the above, as well as other, objects may be realized by a method of analyzing scratches in a region of an optical fiber including providing an array of pixels around a pixel of interest, with the pixel of interest being in a center of the array, averaging intensities of pixels surrounding the pixel of interest, multiplying an averaged intensity by a weighting factor to form a threshold, comparing an intensity of the pixel of interest to the threshold, and flagging the pixel of interest when the intensity of the pixel of interest exceeds the threshold. These steps of providing, averaging, multiplying, comparing and flagging may be repeated for each pixel in the region. The flagged pixels may then be Hough transformed. Features formed by Hough transformed pixels of less than a predetermined linear length may be ignored. The method may include rank filtering features formed by Hough transformed pixels. When more than one feature remains after ignoring short features, the remaining features may be morphologically filtered using a structuring element.

One or more of the above, as well as other, objects may be realized by a method of identifying a feature in a region of a fiber as a scratch including capturing an image of the fiber, Hough transforming features having an intensity exceeding an average intensity in the region by a predetermined amount, thresholding Hough transformed features below a predetermined level, rank filtering Hough transformed features, morphological filtering, when more than one feature remains after said thresholding, closest features using a structuring element, and identifying any features remaining after the morphological filtering and having a length greater than a predetermined length as a scratch. The average intensity may be computed from an array of pixels neighboring a feature. The morphological filtering may include determining a peak value of dimensions in a Hough domain for a feature closed by the structuring element, comparing the peak value to a predetermined multiple of a standard deviation of the dimensions, and ignoring features for which the peak value does not exceed the predetermined multiple of the standard deviation.

One or more of the above, as well as other, objects may be realized by a method of inspecting a fiber including acquiring an image of the fiber, identifying defects in the fiber by intensity variations, rejecting a fiber having any defects in a core region thereof, and subjecting defects in a clad region of the fiber to a two-dimensional discrimination analysis. The two-dimensional analysis may have a cumulative dimension along which a total of the defects is not to exceed a first predetermined value and an individual dimension along which each defect is not to exceed a second predetermined value. A fiber having defects which fail in either dimension will be rejected. The identifying may include determining whether a defect is a blob or a scratch. When the defect is a scratch in the clad region, the individual dimension may be a length of the longest scratch and the cumulative dimension may be a total number of scratches. When the defect is a blob in the clad region, the individual dimension may be an area of the largest blob and a cumulative dimension may be a cumulative blob area. The core region may be defined as some multiple of a core diameter of the fiber. When the fiber is inserted in a supporting structure, the method may include inspecting a layer between the fiber and the supporting structure.

One or more of the above, as well as other, objects may be realized by a method for indicating acceptability of illumination parameters of an optical fiber being illuminated to a user prior to image capture of the optical fiber including displaying scales with ranges for each illumination parameter and displaying an indicator for each image parameter indicating a current value of that illumination parameter. The illumination parameters may be for an end surface of the optical fiber. A green region in each of the scales indicating an acceptable region may be provided.

One or more of the above, as well as other, objects may be realized by a method of initializing an imaging system for a fiber being illuminated including finding an illumination level of the fiber and determining whether the fiber is properly centered in the illumination. Finding the illumination level may include determining an average illumination of the core and an average illumination of the cladding. The acceptability of the contrast and/or the brightness of the fiber may be assessed.

BRIEF DESCRIPTION OF THE DRAWINGS

The foregoing and other objects, aspects and advantages will be described with reference to the drawings, in which:

FIG. 6A illustrates the extraction of the epoxy layer with adjacent regions surrounding the epoxy layer;

FIG. 6B illustrates the region shown in FIG. 6A after unpolarization in accordance with an embodiment of the present invention;

FIG. 6C illustrates the epoxy layer extracted from the region in FIG. 6B;

FIG. 6D is the y-axis projection of the epoxy layer in FIG. 6C;

FIG. 6E is the x-axis projection of the epoxy layer in FIG. 6C;

DETAILED DESCRIPTION OF THE PREFERRED EMBODIMENTS

While the present invention is described herein with reference to illustrative embodiments for particular applications, it should be understood that the present invention is not limited thereto. Those having ordinary skill in the art and access to the teachings provided herein will recognize additional modifications, applications, and embodiments within the scope thereof and additional fields in which the invention would be of significant utility without undue experimentation.

Figure 2:
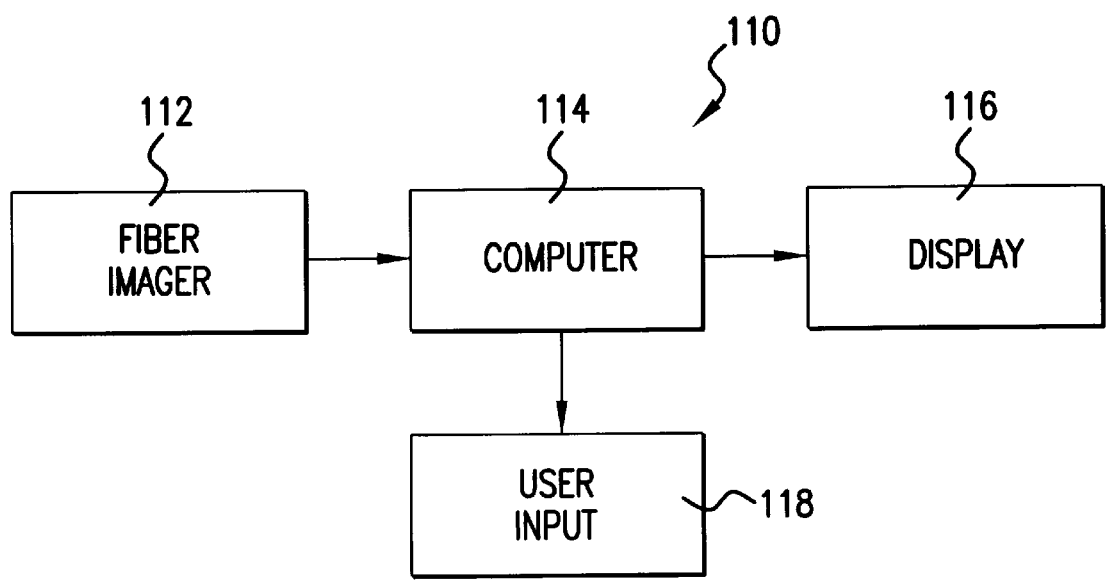
FIG. 2 is a schematic diagram of an inspection system in accordance with the present invention.

FIG. 2 is a schematic illustration of an embodiment of a system 110 used to perform the inspection in accordance with the present invention. The system 110 includes a fiber imager 112, a computer 114, a display 116 and a user input 118. The fiber imager illuminates the fiber to be inspected and captures an image of the illuminated fiber. The fiber imager may be, for example, the imager disclosed in U.S. Pat. No. 5,724,127, which is hereby incorporated by reference in its entirety. The fiber imager 112 provides an image of the optical fiber to the computer 114, which stores and processes the image. The computer 114 displays this image on the display 116. The display 116 represents the image using an array of picture elements (pixels) which typically vary in intensity from 0, representing black, to 255, representing white. The user input 118 may be used to provide information regarding the fiber to be inspected, to begin testing, etc.

Figure 3A:
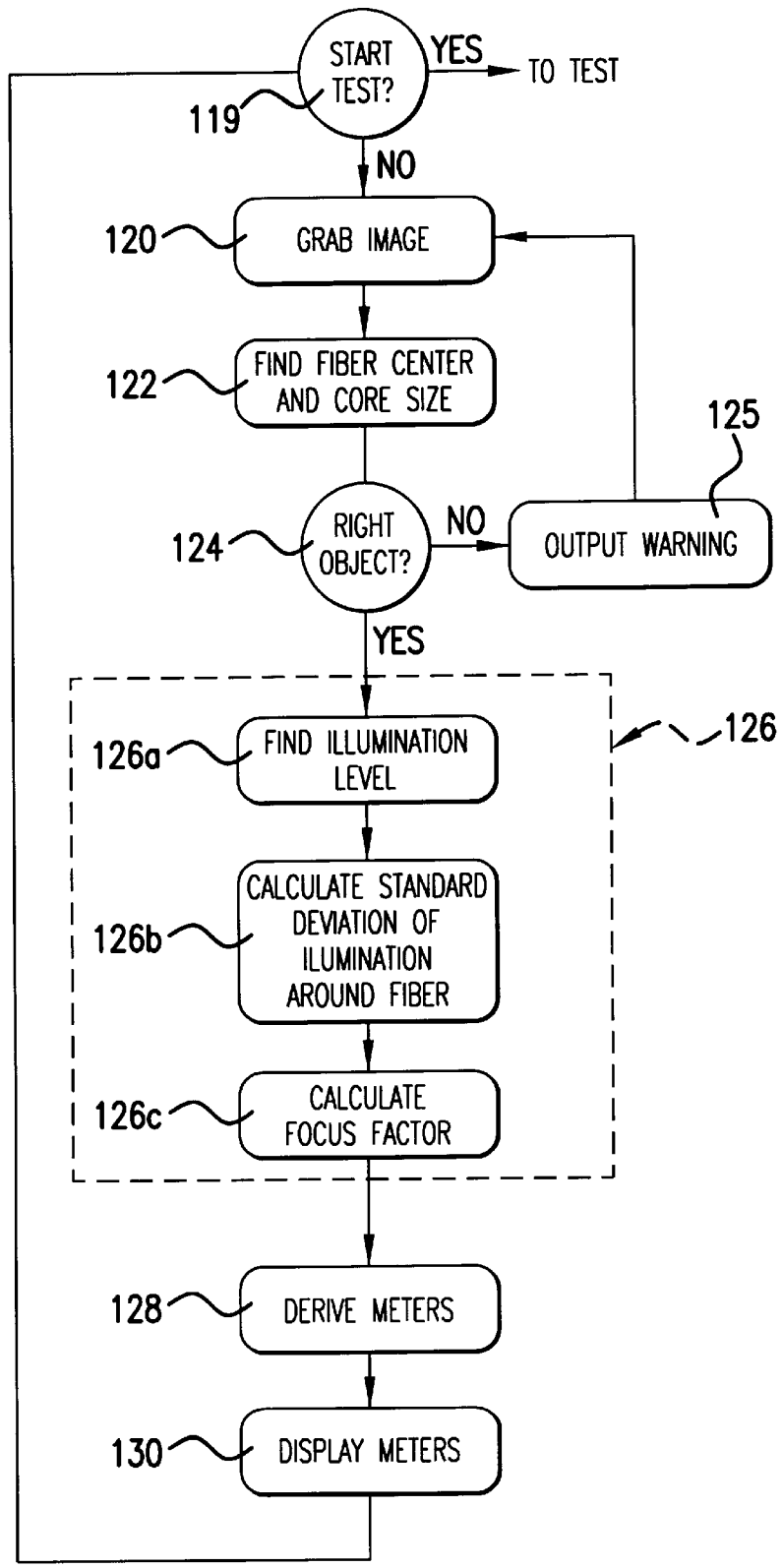
FIG. 3A is a flow chart illustrating a method of initialization for inspection in accordance with the present invention.

FIG. 3A is a flow chart illustrating a method of initializing the inspection. If step 119 determines that the test is not to be started, the method proceeds to step 120. In step 120, the image of the fiber is grabbed by the fiber imager and sent to the computer. The fiber center, the fiber size and the core size are determined by known techniques in step 122. In step 124, the size of the fiber determined in step 122 is compared to a range of fiber sizes to insure that the object being centered on is the fiber. Alternatively, a user may input an expected fiber size and step 124 compares the size determined in step 122 to a range surrounding the expected fiber size to insure that the object being centered on is the fiber. If not, the flow proceeds to step 125 which outputs a warning on the display indicating that the imager is apparently centered on something other than the fiber.

If the fiber diameter is within the expected range, whether predetermined or input, the flow proceeds to section 126 in which the illumination parameters of the fiber are determined. These illumination parameters are then used to derive various meters regarding the illumination of the fiber.

In step 126a, the overall illumination level of the fiber is found. The core and clad zones are extracted and the average pixel level is calculated for each zone. This illumination level is used to normalize the illumination values of other parameters to be determined so that the results of the inspection will not be affected by variations in the illumination level between different inspections. The illumination level may be adjusted by controlling the output of the light source and/or by altering a distance between the light source and the fiber.

In step 126b, the illumination at a number of points, e.g., six, around the edge of each region of the fiber are compared to an average of the illumination at these points in order to determine a standard deviation of illumination around the fiber. In particular, the standard deviation around the core and the standard deviation around the cladding are determined. It is important to insure that the fiber is illuminated as evenly and as directly as possible. If the fiber is illuminated at an angle, one portion of the fiber may overshadow another portion. While image processing can eliminate this shadow, if a defect is present in the shadowed potion, this defect may not appear in the image after the shadow has been removed. Therefore, placing a fiber too far off of the center of illumination can lead to variable results and lower repeatability. Advantageously, the relative position of the fiber and the illumination source is adjusted until the standard deviations are acceptable.

In step 126c, the focus factor is calculated by determining the image intensity gradient. The strength of this image intensity gradient at the fiber edges, e.g., the edge of the core region and the edge of the clad region, serves as the focus factor.

In step 128, a number of meters which are needed to insure a valid inspection in accordance with the present invention are derived based on the illumination parameters acquired in section 126. For example, the acceptability of the position of the fiber is derived based on the standard deviation, where the smaller the deviation, the better the position. A standard deviation around each region of the fiber within, for example, 5%, indicates the fiber is sufficiently centered to insure good repeatability and viewing of all intensity variations. Whether the fiber is in or out of focus is derived based on the focus factor, where the higher the focus factor representing the sharpness at the edges, the more in focus the fiber. The brightness of the overall image is derived from the illumination level, and cannot be so low such that some intensity variations may not be detected or so high such that some intensity variations may be washed out. The contrast is derived based on the illumination averages inside and outside the fiber, and cannot be so high or so low such that some intensity variations may not be detected.

Figure 3B:
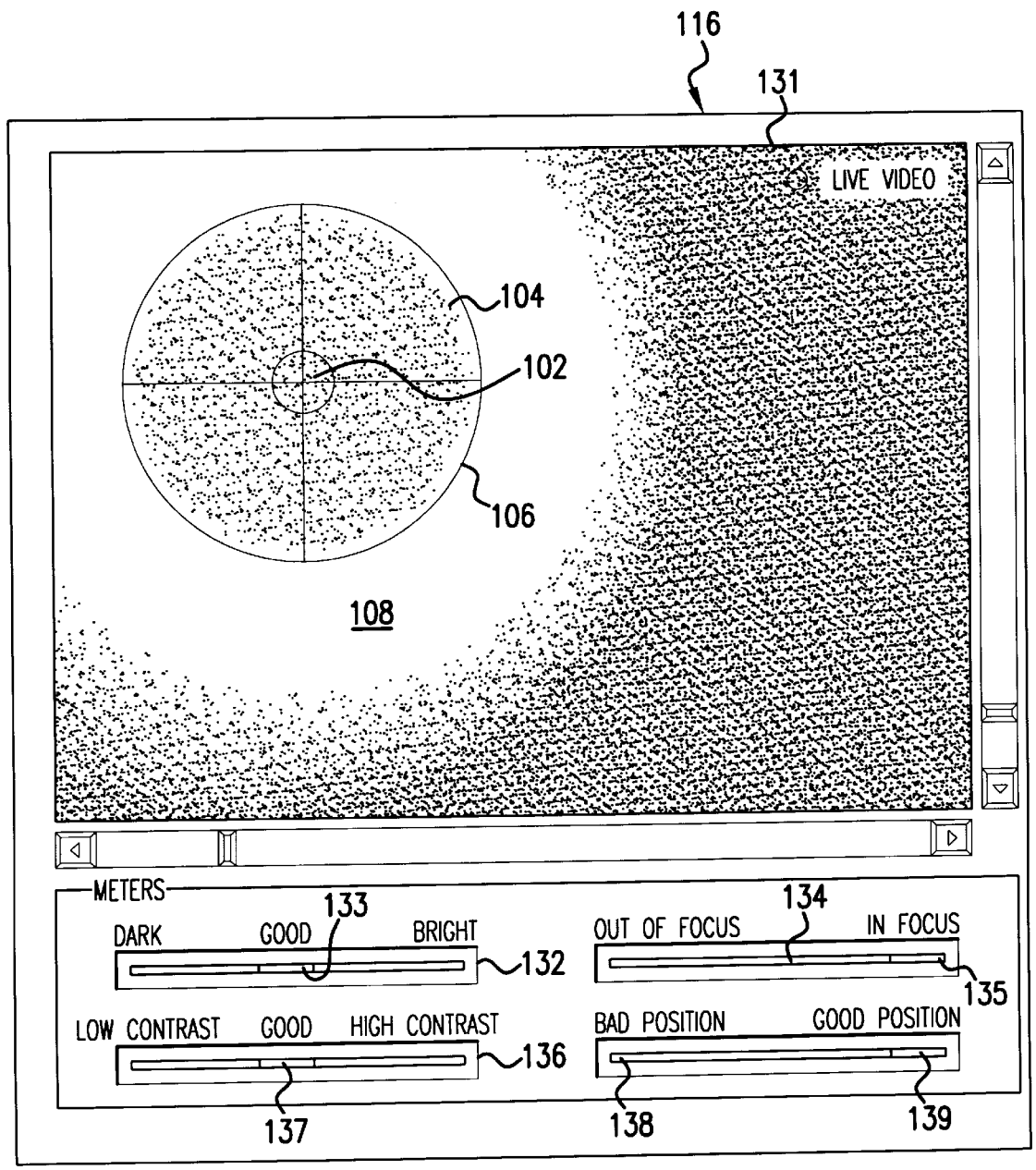
FIG. 3B is a screen displaying meters.

Finally, in step 130, the imaging meters which have been derived may be displayed on the display 116, preferably on relative scales for ease of comprehension by a user. For example, as shown in FIG. 3B, the illumination may be displayed on a scale 132 from "dark" to "bright" with an acceptable region being indicated there between in green, the focus may be displayed on a scale 134 from "out of focus" to "in focus" with an acceptable region near and including the "in focus" end being indicated in green, the contrast may be displayed on a scale 136 from "low contrast" to "high contrast" with an acceptable region being indicated there between in green, and the centering of the fiber relative to the illumination source may be displayed on a scale 138 from "bad position" to "good position" with an acceptable region near and including the "good position" end being indicated in green. The display 116 may also include an image of the fiber itself in a portion 131 of the display.

An indicator 133, 135, 137, 139 for each meter informs the user as to the current values of the imaging parameters on these scales. When each of the indicators is in a corresponding green region, the initialization is complete. If a manual mode of operation has been selected, the user will then adjust the fiber and/or the illumination source in response to any of the meters which were not indicated as being acceptable. If an automatic mode of operation has been selected, the fiber and/or the illumination source are automatically adjusted until all meters are acceptable and the display indicates to the user that the fiber is ready to be inspected.

Figure 4:
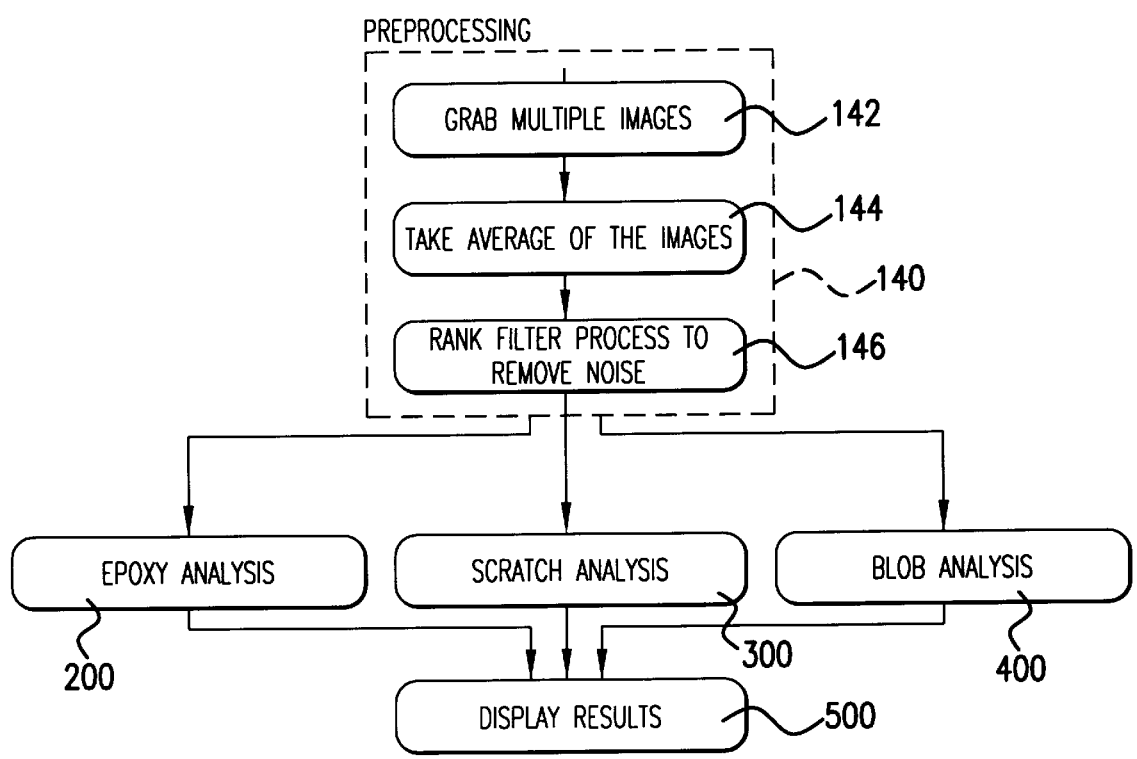
FIG. 4 is a flow chart illustrating the overall flow of the inspection in accordance with the present invention.

If step 119 indicates testing or inspecting is to be started, the method proceeds to the flow chart shown in FIG. 4. The start of inspection may be user initiated or may be automatically instituted upon successful completion of the initialization, i.e., all of the meters are deemed acceptable. The initialization in accordance with the present invention insures repeatability and compensates for any defects in the optical system.

FIG. 4 is a flow chart showing the inspection method in accordance with the present invention. This inspection includes a preprocessing portion 140, an epoxy analysis 200, a scratch analysis 300, a blob analysis 400 and a displaying of results 500.

The preprocessing portion 140 is desirable to remove noise, increase repeatability and/or guarantee image features are the same. The preprocessing portion 140 includes a step 142 of grabbing multiple, e.g., fifteen, images of the fiber under unvarying conditions, a step 144 of averaging the images from step 142, and a step 146 of rank filtering the averaged image from step 144 to remove noise therefrom. This filtered image from step 146 is preferably the one used for the testing portions of the inspection.

While the testing portions shown in FIG. 4 are shown as being performed in parallel, the test may also be run sequentially in any order. Further, while FIG. 4 indicates that all of the tests are performed in a comprehensive mode, if the tests are performed sequentially and a user does not want all available information regarding the optical fiber but only cares if the fiber is acceptable, as soon as one of the criteria discussed below is not met, the inspection can proceed to the display step 500 and indicate that the fiber is unacceptable. Any subsequent references to a comprehensive mode in which all tests are performed are to be understood in relation to sequential processing only.

Figure 1:
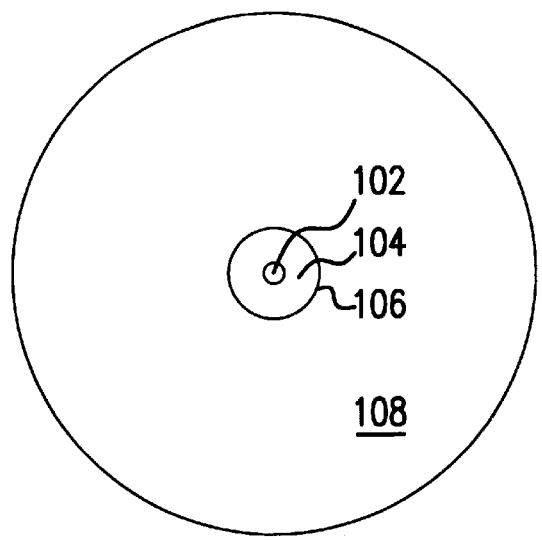
FIG. 1 is a cross-section of an optical fiber in a ferrule.

The first test shown in FIG. 4, the epoxy analysis 200, is a unique concept to the inspection of the present invention. When fibers are inserted into ferrules or other supporting structures, as shown in FIG. 1, they inevitably do not fit perfectly therein. In order to eliminate a resulting air gap between the fiber and the ferrule, as well as to secure the fiber to the ferrule, an epoxy is applied to form the epoxy layer 106. Evidence shows that failure of the epoxy layer 106 to be evenly distributed around the fiber is one key reason which gives rise to the problem of optical connector reliability.

Two fundamental failure modes are generated from uneven or inappropriate epoxy distribution. The first failure mode occurs along the fiber axis and results in permanent fiber withdrawal of up to 100 nm (according to Bellcore/TCA 1996 analysis of fiber optic reliability standard workgroup). The second failure mode occurs in the plane perpendicular to the fiber axis and results in lateral air gaps and stresses which contribute to accelerated cracking and fissure of the fiber media. These failure modes are further accelerated by environmental and mechanical stresses encountered by the fiber in use, such as changes in pressure, humidity, temperature, etc. Previous inspection methods discard image data from the transition zone between the cladding and the ferrule or other supporting structure. In accordance with the present invention, this data is used to analyze the epoxy layer as a further key parameter of interest in assessing long term reliability of an optical fiber as discussed below.

Figure 5:
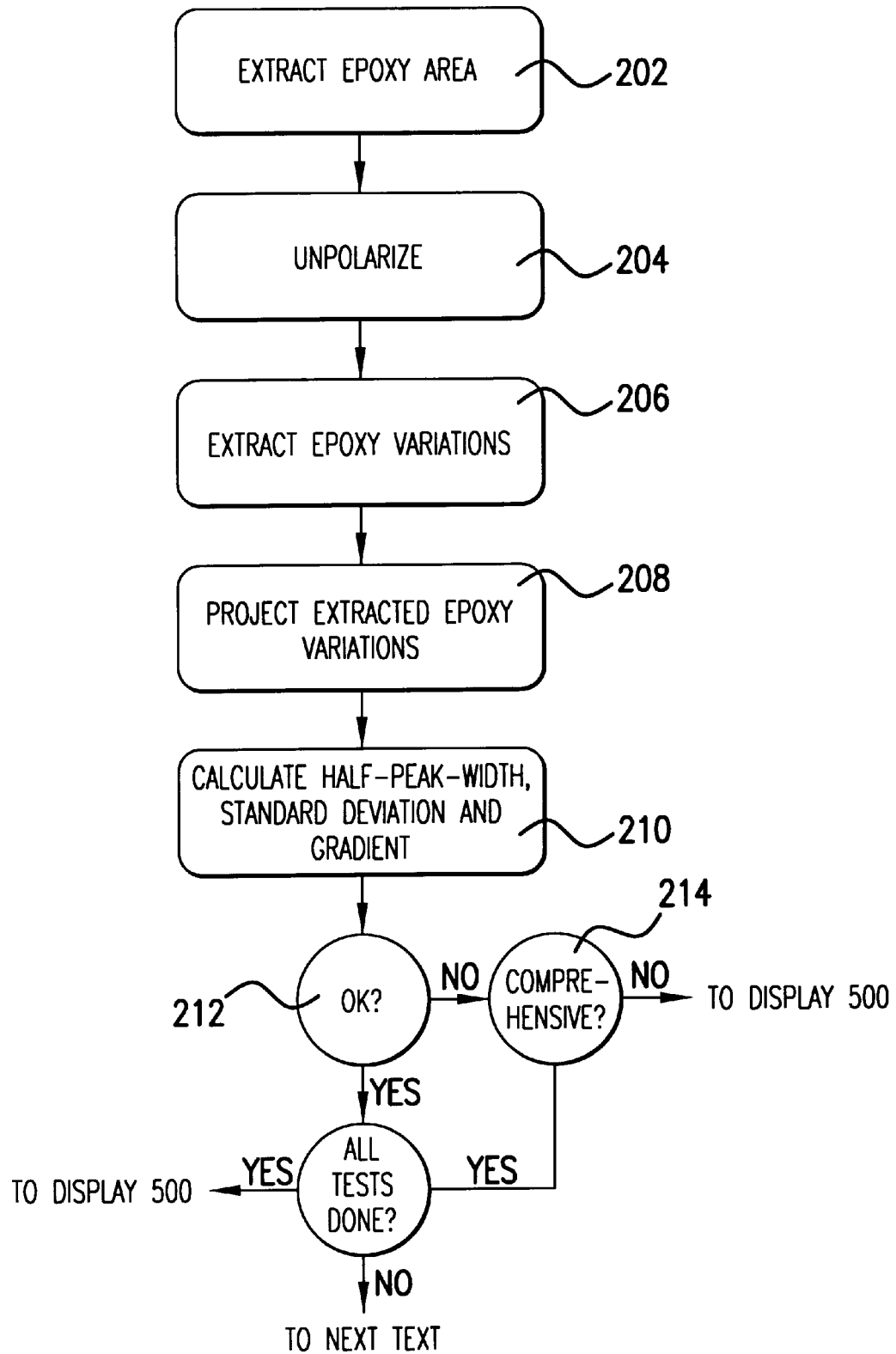
FIG. 5 is a flow chart illustrating a method for inspecting the epoxy layer in accordance with an embodiment of the present invention.

FIG. 5 is a flow chart illustrating a method of inspecting the epoxy area of an optical fiber, such as the optical fiber shown in FIG. 1. As can be seen therein, this inspecting method involves extracting the epoxy area in step 202, unpolarizing the extracted epoxy area in step 204, extracting the epoxy layer from the unpolarized area in step 206, projecting the extracted epoxy layer in step 208, and calculating a standard deviation and gradient at step 210. Each of these steps will be discussed in detail below.

When imaged, the epoxy area is darker than the ferrule, which is bright white. The computer 114 may extract the epoxy area in accordance with step 202 by determining where this boundary indicated by the dark epoxy area is located or by assuming this epoxy is at the periphery of a perfectly circular fiber having the fiber diameter and center determined in the initialization. A predetermined amount, e.g., eight pixels, of image data on either side of this boundary are also extracted. A number of pixels are needed since the epoxy layer varies in thickness and to account for imperfections in the circularity of the fiber. FIG. 6A illustrates the annulus 250 resulting from this extraction. The annulus 250 contains all of the image data of the epoxy area in area 252, as well as image data from the clad region adjacent the epoxy area in area 254 and image data from the ferrule region adjacent the epoxy area in area 256. Typically, the inner ring of the annulus 250 sufficient to capture the epoxy area will have a diameter of approximately 90% of the fiber diameter and the outer ring of the annulus 250 will have a diameter of approximately 110% of the fiber diameter.

The computer 114 then can "unpolarize" this extracted data in accordance with step 204, i.e., project the annulus resulting from the extraction as shown in FIG. 6A into a linear representation as shown in FIG. 6B. From this linear representation, the computer 114 can then extract the epoxy region 252 from the linear image in accordance with step 206 by extracting the intensities which are lower than the intensity in the bright ferrule region and which vary from the intensity of the clad region. FIG. 6C illustrates the extracted epoxy layer 252.

While the epoxy region 252 is shown as a layer having an even thickness in FIGS. 6A and 6B, in practice and as shown in FIG. 6C, the epoxy will vary in thickness. Therefore, in order to most readily assess how much the thickness is varying by along the layer, the extracted epoxy region is projected in accordance with step 208 along the y-axis into a plot of thicknesses centered on the average thickness T as shown in FIG. 6D and along the x-axis as shown in FIG. 6E, where the bottom line represents a thickness of zero. The smoothness of the distributions in FIG. 6C–6E will depend upon the number of sampling points taken along the x-axis.

Once the distribution of the thickness has been generated as shown in FIG. 6D and 6E, various parameters describing the distribution may be determined in accordance with statistical analysis principles. For example, in accordance with step 210, the half-peak-width, i.e., the width of the distribution where the number of occurrences falls off to half of the peak occurrences, of the y-axis projection, the standard deviation of the x-axis projection, and gradients of the x-axis projection, i.e., $\Delta y/\Delta x$, are determined. All of the noted parameters provide information regarding the shape of the distribution.

An example of the criteria used in evaluating this distribution is as follows. The half peak width of the y-axis projection should be less than some percentage, e.g., 0.5–20%, of the fiber diameter. The standard deviation of the x-axis projection should be less than some percentage, e.g., 0.5–20% of the fiber diameter. The maximum gradient of the x-axis projection should be less than the tangent of an angle indicating significant slope, e.g., an angle greater than between 30° and 60°. If any one of these criteria is not met, then the fiber will fail.

Step 212 assesses whether the fiber has failed the epoxy test or not. If the fiber has failed the epoxy test, step 214 determines whether the system is operating in a comprehensive mode. If the system is not operating in the comprehensive mode, the result that the fiber has failed the inspection is output to the display step 500. If the system is operating in the comprehensive mode or if the fiber has passed the epoxy analysis, step 216 determines whether all steps have been performed. If not, the inspection proceeds to the next test. If all tests have been completed, the inspection proceeds to the display step 500.

The inspection of the present invention also examines the core and cladding regions for intensity variations therein. These intensity variations fall into two general categories, scratches and blobs. Scratches are usually very straight and have a higher intensity than the surrounding area. For the inspection in accordance with the present invention, a scratch is defined as a linear feature having a predetermined minimum length that is wide enough to be detected by the optical power of the inspection system. This minimum length is determined in accordance with a desired sensitivity of the inspection. A blob is any non-uniform distribution of light intensity other than a scratch, including pits, chips, cracks, dirt, etc.

In accordance with the present invention, the inspection analyzes a core region or zone, including and extending beyond the core, and a clad region or zone for defects. This is to account for the fact that the closer to the core a defect occurs, the more intolerable the defect, while only requiring two sets of decision criteria. There are different levels of acceptable presence of discontinuities for the core region and the clad region. In accordance with a preferred embodiment, the core region is some multiple, e.g., 1.5–25, times the diameter of the core from the center of the fiber, and the cladding region is defined by an annulus having an inner diameter which is the diameter of the core region and an outer diameter which is approximately 90% of the diameter of the fiber. The larger the core region, which has stricter criteria than the clad region, the more likely a fiber will be to fail the inspection. Similarly, the larger the outer diameter of the clad region, the more likely the fiber will fail inspection. Thus, the determination of these regions is based on the strictness of the inspection desired. When either of these tests is to be performed, the pixels in both regions are scanned in one pass and stored for use in the respective analyses.

Figure 7:
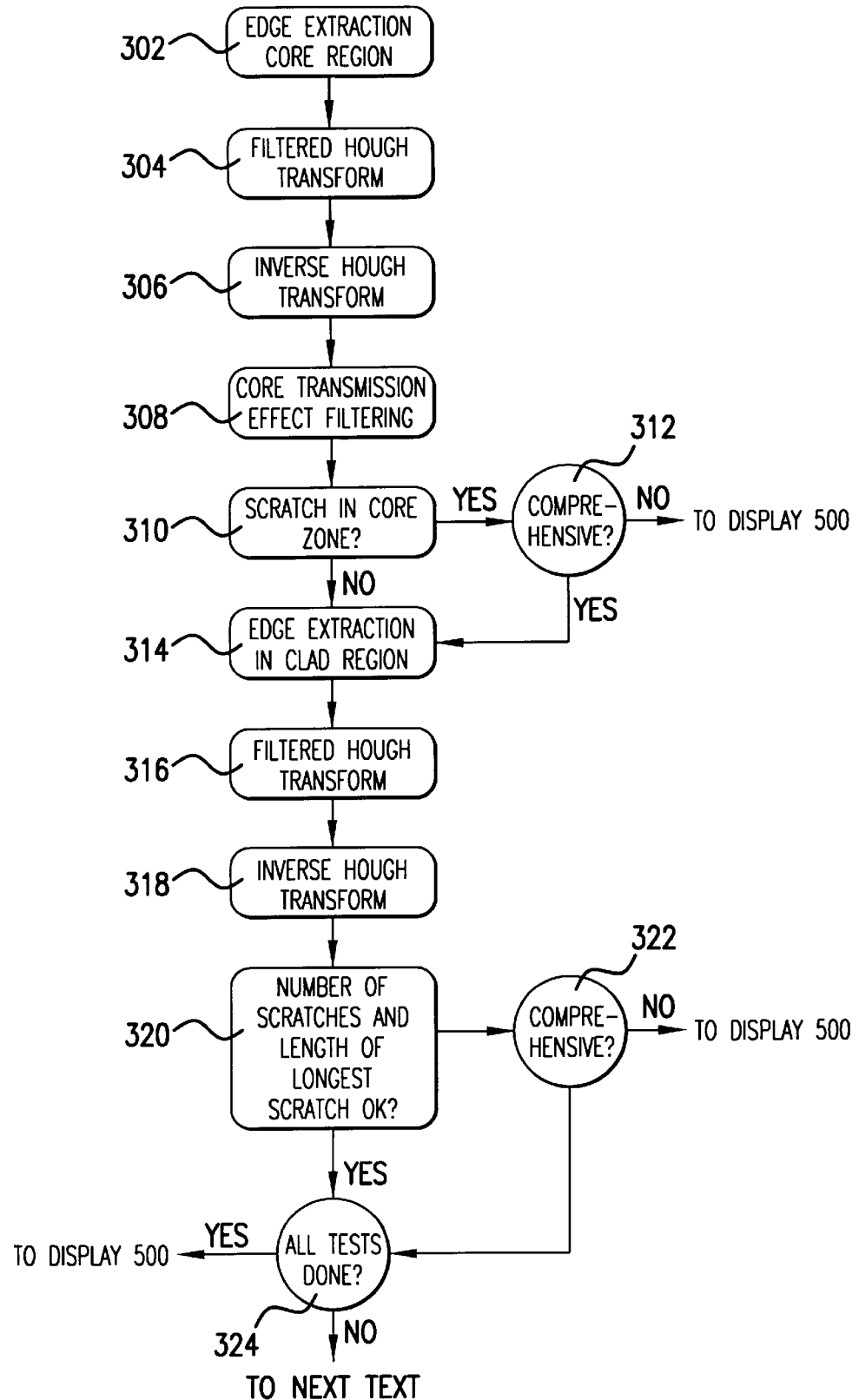
FIG. 7 is a flow chart illustrating a method for analyzing scratches on the fiber in accordance in the present invention.

FIG. 7 is a flow chart illustrating the details of the scratch analysis 300 in accordance with the present invention. Step 302 performs an edge extraction in the following manner. An array of pixels, e.g., three by three pixels, is arranged having a pixel of interest in the center thereof. The intensities of the non-central pixels are averaged. If the center pixel has an intensity greater than the averaged intensity times a weighting value, the pixel is flagged as being part of an edge. Otherwise, the pixel does not constitute an edge. The weighting value may vary in accordance with a desired sensitivity, but may be, for example, 200. Such an edge extraction scheme addresses the problem of dealing with the transition zone between the core and the cladding that is part of the core zone, such that this transition zone will not qualify as an edge.

In step 304, the edges extracted by the step 302 are subjected to a filtered Hough transform so that presence of valid scratches may be determined. A Hough transform converts features from a spatial domain into a domain in which a feature is represented by its radial distance and angle from a set reference point. These values are then binned, such that a straight line, which have many points with similar radial distances and angles, will appear in the same bin, forming a spot in the transformed domain. These binned values are subjected to a hard thresholding to eliminate all bins without a sufficient number of points to qualify as a possible scratch. The number of points in this domain indicates the length of the edge, with the hard threshold being the number required being the number needed for the predetermined minimum length. After the hard thresholding, the binned values are also rank filtered to remove noise and smooth the data.

If there is more than one bin remaining after the hard thresholding, the remaining bins must be analyzed to determine whether each is a separate scratch. For example, a thick line or a long line may appear as more than one line. Alternatively, not all blobs may have been eliminated by the edge extraction. To help compensate for these potential discrepancies, bins that are close to one another are subjected to morphological filtering. The morphological filtering closes regions that are close enough to each other based on structuring elements, e.g., a rectangle. Bins within a closed region are connected to form a single feature. If a peak value for the radius and angle for the single feature is not greater than some multiple, e.g., 2–4.5, of the standard deviation of the radius and angle, this single feature is more likely to be a blob, and is eliminated from consideration as a scratch.

Any features which are not eliminated by the filtering in the filtered Hough transform step 304 are inverse Hough transformed at step 306 so that the scratches can be inspected and/or visualized by a user. These scratches may then again be assessed to determine if they are of sufficient length. Step 308 then performs a core transmission effect filtering to eliminate any remaining features below an illumination threshold due to scattered or direct illumination, as a scratch will be very bright after the inverse Hough transform. If step 310 determines that there are any scratches in the core zone, the fiber fails the core scratch test. If the fiber fails the core scratch test, step 312 determines whether the comprehensive mode is in use. If not, the inspection indicates to the display step 500 that the fiber has failed. If the comprehensive mode is used or there are no scratches in the core zone, the inspection proceeds to analyzing scratches in the clad zone. While the clad zone scratch test has been shown as following the core zone scratch test, these tests may proceed in parallel or in any order relative to the other tests.

While the clad zone in accordance with the present invention is outside the core-cladding transition zone, a clad zone edge extraction step 314 needed to insure that the epoxy layer is not inadvertently considered to be a scratch. The clad zone edge extraction 314 is the same as the core zone edge extraction discussed above, although a different weighting value could be used. The edges are subjected to a filtered Hough transformed in step 316 in a similar manner as discussed above regarding step 304. The scratches not eliminated by the filtered Hough transform of step 316 are inverse Hough transformed in step 318.

Figure 8:
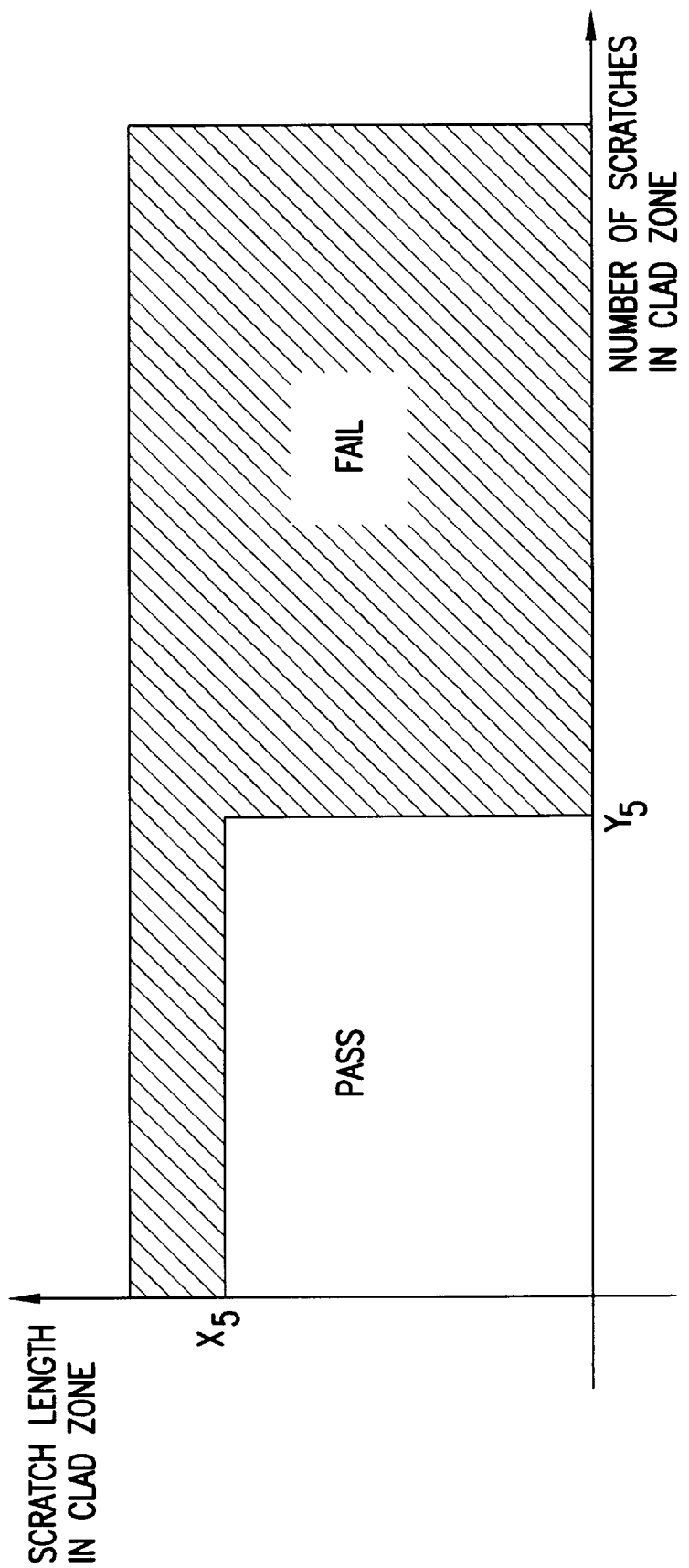
FIG. 8 is a plot illustrating an example of the decision criteria regarding scratches in the cladding region in accordance with an embodiment of the present invention.

Step 320 determines the number of scratches in the clad zone and the length of the longest scratch in the clad zone. An example of the criteria used to determine if these scratches are acceptable is shown in FIG. 8. If the longest scratch in the clad zone equals or exceeds $x_s$, the fiber will fail the clad zone scratch test. Additionally, if there are more than $y_s$ scratches in the clad zone, the fiber will fail the clad zone scratch test. The selection of $x_s$ and $y_s$ depends upon the desired selectivity of the inspection. The smaller $x_s$ or $y_s$, the tougher the criteria, so the more selective the inspection, i.e., more fibers will fail the clad zone scratch test and be rejected. As an example, the length $x_s$ which the longest scratch must be less than may be equal to some multiple, e.g., 0.5–10, of the core diameter, and the number of scratches $y_s$ may be, e.g., 2–20.

If the fiber fails, step 322 determines whether the comprehensive mode is in use. If not, the inspection indicates to the display step 500 that the fiber has failed. If the comprehensive mode is used or the fiber has an acceptable level of scratches in the clad zone, step 324 determines whether all tests have been completed. If not, the inspection proceeds to the next test. If all tests have been completed, the inspection proceeds to the display step 500.

Figure 9:
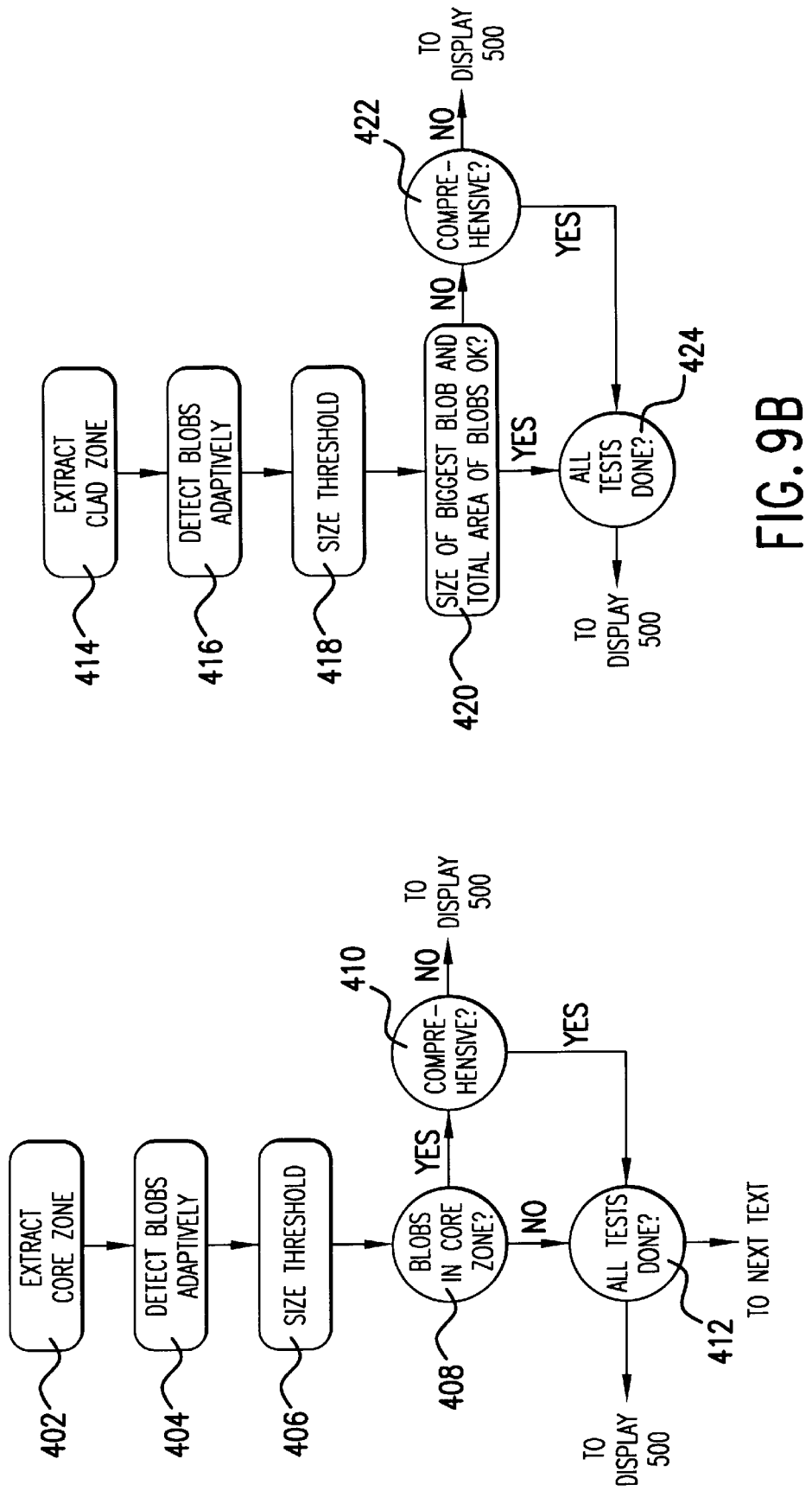
FIG. 9A is a flow chart illustrating a method for analyzing blobs on the core zone of the fiber in accordance in the present invention.
FIG. 9B is a flow chart illustrating a method for analyzing blobs on the clad zone of the fiber in accordance in the present invention.

FIG. 9A is a flow chart illustrating the blob analysis for the core zone in accordance with the present invention. Step 402 extracts the core zone and preferably includes core discrimination in which the average illumination in the core itself is subtracted from the pixels in the core itself. Since the following blob test is based on deviations from the average intensity, the core discrimination removes the bias of the illumination of the core itself. For example, if the core is bright, bright blobs may not be detected.

Step 404 detects potential blobs adaptively by searching for regions within the core zone which vary, either above or below, in intensity from the local average intensity by a predetermined amount. The predetermined amount may be set based on a desired sensitivity, and is preferably some multiple, e.g., 0.5–1.5, of the local standard deviation. The number of adjacent or neighboring pixels that constitute the local area considered in the adaptive detection is a trade-off between speed and the needed sensitivity. Step 406 then size thresholds the regions from step 404 to eliminate scratches and noise. Step 408 determines if there are any blobs in the core zone after the size threshold of step 406. If there are blobs in the core zone, the fiber will fail the core zone blob test.

If the fiber fails the core blob test, step 410 determines whether the comprehensive mode is in use. If not, the inspection indicates to the display step 500 that the fiber has failed. If the comprehensive mode is used or there are no blobs in the core zone, step 412 determines whether all of the tests have been performed. If not, the inspection proceeds to the next test. If all tests have been completed, the inspection outputs the results to the display 500.

FIG. 9B is a flow chart illustrating the blob analysis for the clad zone. Step 414 extracts the clad zone. Step 416 adaptively detects potential blobs by searching for regions within the clad zone which vary from the local average intensity by a predetermined amount. The predetermined amount may be set based on a desired sensitivity, and is preferably some multiple, e.g., 0.5–1.5, of the local standard deviation. The number of adjacent or neighboring pixels that constitute the local area considered in the adaptive detection is a trade-off between speed and the needed sensitivity. Step 418 then size thresholds the regions from step 416 to eliminate scratches and noise, e.g., the blob must be more than a few pixels wide, or whatever the expected width of the widest scratch. Step 420 determines the size of the biggest blob and the total area of all of the blobs from step 418.

Figure 10:
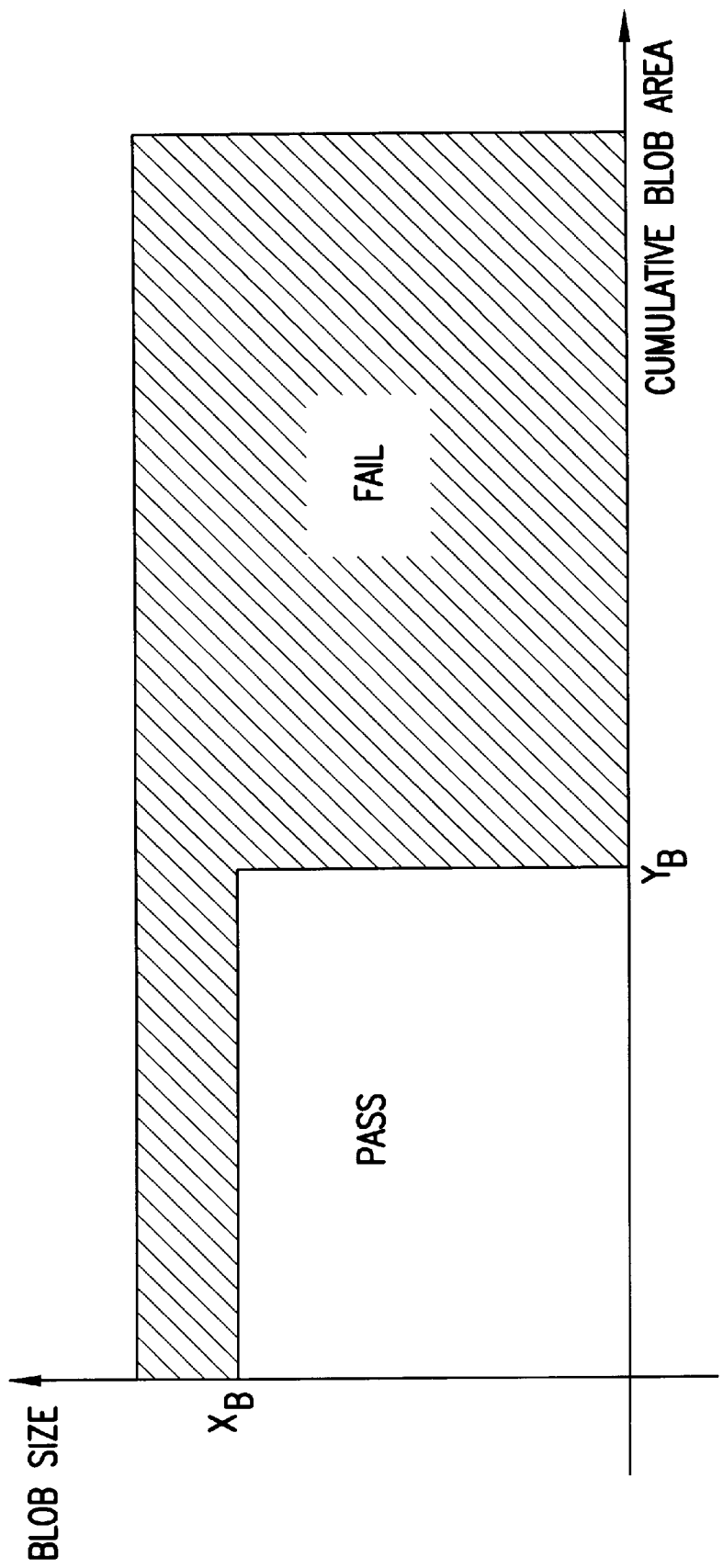
FIG. 10 is a plot illustrating an example of the decision criteria regarding blobs in the cladding region in accordance with an embodiment of the present invention.

An example of the criteria used to determine if these parameters are acceptable is shown in FIG. 10. If the biggest blob in the cladding region exceeds $x_b$, the fiber will fail the clad zone blob test. Additionally, if the total area of all of the blobs within the clad zone exceeds $y_b$, the fiber will fail the clad zone blob test. The selection of $x_b$ and $y_b$ depends upon the desired selectivity of the inspection. The smaller $x_b$ or $y_b$, the tougher the criteria, so the more selective the inspection, i.e., more fibers will fail the clad zone blob test and be rejected. Obviously, for the criteria $y_b$ to be meaningful, it needs to be larger than $x_b$. As an example, the largest blob size may not exceed a multiple, e.g., 0.25–5, of the core area, and the cumulative blob area may not exceed a multiple, e.g., 0.5–15, of the core area.

If the fiber fails, step 422 determines whether the comprehensive mode is in use. If not, the inspection indicates to the display step 500 that the fiber has failed. If the comprehensive mode is used or the fiber has an acceptable level of scratches in the cladding region, step 424 determines whether all tests have been completed. If not, the inspection proceeds to the next test. If all tests have been completed, the inspection proceeds to the display step 500.

Once all of the tests have been completed, or once the fiber has failed any of the tests when not in the comprehensive mode, the inspection proceeds to the display step 500. In the display step 500, the end result of the fiber passing or failing is indicated, with or without indication as to which test the fiber failed. If in the comprehensive mode, the display can also indicate the pass/fail status for each test. One of ordinary skill in the art would realize that any number of displays which alerts the user to the acceptability of the fiber, including audible as well as visual indication, can be used.

As described above, the inspection in accordance with the present invention has numerous advantages. A definitive answer is provided to a user. The evenness of the distribution of the epoxy between the fiber and the supporting structure can be analyzed. The extent of scratches and blobs in the cladding zone can be analyzed without requiring extensive classification of each type of defect. Scratches can be readily assessed in the core and clad zones. The automated assessment of the clad region accounts for both a cumulative effect of each type of defect as well as a maximum parameter for a single defect, both of which must be met for the fiber to pass. Assessing the acceptability of illumination parameters during initialization prior to beginning inspection improves repeatability and accounts for any defects in the optics of the inspection system. Repeatability may also be increased by insuring centering of illumination and/or averaging successive images.

Although preferred embodiments of the present invention have been described in detail herein above, it should be clearly understood that many variations and/or modifications of the basic inventive concepts taught herein, which may appear to those skilled in the art, will still falls within the spirit and scope of the present invention as defined in the appended claims and their equivalents.

Having thus described our invention, what we claim as new and desire to secure by Letters Patent is as follows:

1. A method for inspecting an optical fiber in a supporting structure comprising:

analyzing a distribution of an entire epoxy layer between the optical fiber and the supporting structure; and determining acceptability of the optical fiber in accordance with the distribution of the entire epoxy layer.

2. The method of claim 1, wherein said analyzing includes imaging the entire epoxy layer.

3. The method of claim 2, wherein the supporting structure is a ferrule and said imaging includes imaging at least a portion of the ferrule and the entire epoxy layer.

4. The method of claim 2, wherein said analyzing further comprises unpolarizing an image of an annulus formed by the epoxy layer.

5. The method of claim 1, wherein said analyzing includes calculating statistical parameters regarding variations in thickness of the epoxy layer around the optical fiber.

6. The method of claim 5, wherein said statistical parameters include at least one of a half-peak width of a distribution of thicknesses of the epoxy layer, a standard deviation of the thicknesses of the epoxy layer, and a maximum gradient of thickness variations in the epoxy layer.

7. A method for determining centering of an optical fiber relative to an illumination source comprising:

comparing illumination levels between at least three points around a periphery of the optical fiber; and determining whether centering of the optical fiber relative to the illumination source is within a predetermined level.

8. The method of claim 7, further comprising, when said determining indicates that the centering is not within the predetermined level, moving the optical fiber and the illumination source relative to one another.

9. The method of claim 7, wherein said determining includes generating a standard deviation between an average of the illumination levels at the at least three points.

10. A method of analyzing scratches in a region of an optical fiber comprising:

a) providing an array of pixels around a pixel of interest, with the pixel of interest being in a center of the array;

b) averaging intensities of pixels surrounding the pixel of interest;

c) multiplying an averaged intensity by a weighting factor to form a threshold;

d) comparing an intensity of the pixel of interest to the threshold and flagging the pixel of interest when the intensity of the pixel of interest exceeds the threshold; and e) repeating said providing, averaging, multiplying and comparing for each pixel in the region.

11. The method of claim 10, further comprising Hough transforming flagged pixels.

12. The method of claim 11, further comprising ignoring features formed by Hough transformed pixels of less than a predetermined linear length.

13. The method of claim 11, further comprising, rank filtering features formed by Hough transformed pixels.

14. The method of claim 12, further comprising, when more than one feature remains after said ignoring, morphologically filtering features formed by Hough transformed pixels using a structuring element.

15. A method of identifying a feature in a region of a fiber as a scratch comprising:

capturing an image of the fiber;

Hough transforming features having an intensity exceeding an average intensity in the region by a predetermined amount;

thresholding Hough transformed features below a predetermined level;

rank filtering Hough transformed features;

morphological filtering, when more than one feature remains after said thresholding, closest features using a structuring element; and identifying any features remaining after said morphological filtering and having a length greater than a predetermined length as a scratch.

16. The method of claim 15, further comprising computing the average intensity from an array of pixels neighboring a feature.

17. The method of claim 15, wherein said morphological filtering includes determining a peak value of dimensions in a Hough domain for a feature closed by said structuring element, comparing the peak value to a predetermined multiple of a standard deviation of the dimensions, and ignoring features for which the peak value does not exceed the predetermined multiple of the standard deviation.

18. A method of inspecting a fiber comprising:

acquiring an image of the fiber;

identifying defects in the fiber by intensity variations;

rejecting a fiber having any defects in a core region thereof; and subjecting defects in a clad region of the fiber to a two-dimensional discrimination analysis, said two-dimensional analysis having a cumulative dimension along which a total of the defects is not to exceed a first predetermined value and an individual dimension along which each defect is not to exceed a second predetermined value, and rejecting a fiber having defects which fail in either dimension.

19. The method of claim 18, wherein said identifying includes determining whether a defect is a blob or a scratch.

20. The method of claim 19, wherein when a defect is a scratch in the clad region, the individual dimension is a length of the longest scratch and the cumulative dimension is a total number of scratches.

21. The method of claim 19, wherein when a defect is a blob in the clad region, the individual dimension is an area of the largest blob and a cumulative dimension is a cumulative blob area.

22. The method of claim 18, further comprising defining the core region as some multiple of a core diameter of the fiber.

23. The method of claim 18, further comprising, when the fiber is inserted in a supporting structure, inspecting a layer between the fiber and the supporting structure.

24. A method for indicating acceptability of illumination parameters of an optical fiber being illuminated to a user prior to image capture of the optical fiber comprising displaying scales with ranges for each illumination parameter and displaying an indicator for each image parameter indicating a current value of that illumination parameter.

25. The method of claim 24, wherein the illumination parameters are for an end surface of the optical fiber.

26. The method of claim 24, further comprising providing a visibly different region in the each of the scales indicating an acceptable region.

27. A method of initializing an imaging system for a fiber being illuminated comprising:

finding an illumination level of the fiber;

determining whether the fiber is properly centered in the illumination; and normalizing parameters to be analyzed in accordance with the illumination level.

28. The method of claim 27, wherein finding the illumination level includes determining an average illumination of the core and an average illumination of the cladding.

29. The method of claim 27, further comprising determining whether contrast of the fiber is acceptable.

30. The method of claim 27, further comprising determining whether brightness of the fiber is acceptable.

* * * * *